(12) United States Patent
Curley

(10) Patent No.: US 9,937,000 B2
(45) Date of Patent: Apr. 10, 2018

(54) METHODS AND DEVICES FOR CONTROLLING ABLATION THERAPY

(71) Applicant: Thermedical, Inc., Waltham, MA (US)

(72) Inventor: Michael G. Curley, Weston, MA (US)

(73) Assignee: Thermedical, Inc., Waltham, MA (US)

( * ) Notice: Subject to any disclaimer, the term of this patent is extended or adjusted under 35 U.S.C. 154(b) by 0 days.

(21) Appl. No.: 15/240,693

(22) Filed: Aug. 18, 2016

(65) Prior Publication Data

US 2016/0354138 A1 Dec. 8, 2016

Related U.S. Application Data

(62) Division of application No. 13/445,373, filed on Apr. 12, 2012.

(Continued)

(51) Int. Cl.
*A61B 18/04* (2006.01)
*A61B 18/08* (2006.01)
(Continued)

(52) U.S. Cl.
CPC .......... *A61B 18/04* (2013.01); *A61B 18/082* (2013.01); *A61B 18/1477* (2013.01); *A61B 2017/00526* (2013.01); *A61B 2018/00029* (2013.01); *A61B 2018/00577* (2013.01); *A61B 2018/00642* (2013.01); *A61B 2018/00773* (2013.01);
(Continued)

(58) Field of Classification Search
CPC .. A61N 1/3943; A61N 1/3987; A61N 1/3704; A61N 1/3756; A61N 1/0504; A61N 1/3925; A61B 5/0468
See application file for complete search history.

(56) References Cited

U.S. PATENT DOCUMENTS 4,160,455 A 7/1979 Law
4,424,190 A 1/1984 Mather, III et al.
(Continued)

FOREIGN PATENT DOCUMENTS

CN 1341462 A 3/2002
CN 1119127 C 8/2003
(Continued)

OTHER PUBLICATIONS

Chinese Office Action for Application No. 201380053690.0, dated Sep. 30, 2016. (17 pages).
(Continued)

*Primary Examiner* — Rex R Holmes
(74) *Attorney, Agent, or Firm* — Nutter McClennen & Fish LLP

(57) ABSTRACT

Devices and methods for controlling ablation therapy are provided herein. In one embodiment, an ablation device is provided that includes an elongate body having proximal and distal ends, and an inner lumen extending therethrough. The inner lumen can be configured to receive fluid therein and to deliver fluid to the distal end of the elongate body. The device can also include an ablation element positioned at a distal end of the elongate body that is configured to heat surrounding tissue, and a heater element disposed within the inner lumen adjacent to a distal end of thereof, the heater element being configured to heat fluid flowing through the inner lumen.

22 Claims, 4 Drawing Sheets

Related U.S. Application Data

(60) Provisional application No. 61/474,574, filed on Apr. 12, 2011.

(51) Int. Cl.
*A61B 18/14* (2006.01)
*A61B 18/00* (2006.01)
*A61B 17/00* (2006.01)

(52) U.S. Cl.
CPC .............. *A61B 2018/00791* (2013.01); *A61B 2018/00797* (2013.01); *A61B 2018/00809* (2013.01); *A61B 2018/00821* (2013.01); *A61B 2018/046* (2013.01); *A61B 2018/1425* (2013.01); *F04C 2270/041* (2013.01); *Y10T 29/49016* (2015.01); *Y10T 29/49085* (2015.01)

(56) References Cited

U.S. PATENT DOCUMENTS

| | | |
|---|---|---|
| 5,190,538 A | 3/1993 | Hussein et al. |
| 5,271,413 A | 12/1993 | Dalamagas et al. |
| 5,336,222 A | 8/1994 | Durgin, Jr. et al. |
| 5,403,311 A | 4/1995 | Abele et al. |
| 5,409,487 A | 4/1995 | Jalbert et al. |
| 5,431,648 A | 7/1995 | Lev |
| 5,431,649 A | 7/1995 | Mulier et al. |
| 5,437,629 A | 8/1995 | Goldrath |
| 5,437,673 A * | 8/1995 | Baust .......... A61F 7/12 604/30 |
| 5,449,380 A | 9/1995 | Chin |
| 5,456,682 A | 10/1995 | Edwards et al. |
| 5,458,597 A | 10/1995 | Edwards et al. |
| 5,462,521 A | 10/1995 | Brucker et al. |
| 5,472,441 A | 12/1995 | Edwards et al. |
| 5,496,271 A | 3/1996 | Burton et al. |
| 5,522,815 A | 6/1996 | Durgin, Jr. et al. |
| 5,545,195 A | 8/1996 | Lennox et al. |
| 5,549,559 A | 8/1996 | Eshel |
| 5,609,151 A | 3/1997 | Mulier et al. |
| 5,653,692 A | 8/1997 | Masterson et al. |
| 5,728,143 A | 3/1998 | Gough et al. |
| 5,735,846 A | 4/1998 | Panescu et al. |
| 5,800,482 A | 9/1998 | Pomeranz et al. |
| 5,827,269 A | 10/1998 | Saadat |
| 5,891,094 A | 4/1999 | Masterson et al. |
| 5,891,134 A | 4/1999 | Goble et al. |
| 5,944,713 A | 8/1999 | Schuman |
| 5,954,719 A | 9/1999 | Chen et al. |
| 5,964,791 A | 10/1999 | Bolmsjo |
| 6,024,743 A | 2/2000 | Edwards |
| 6,030,379 A | 2/2000 | Panescu et al. |
| 6,032,077 A | 2/2000 | Pomeranz |
| 6,033,383 A | 3/2000 | Ginsburg |
| 6,045,549 A | 4/2000 | Smethers et al. |
| 6,056,746 A | 5/2000 | Goble et al. |
| 6,071,280 A | 6/2000 | Edwards et al. |
| 6,080,151 A | 6/2000 | Swartz et al. |
| 6,090,106 A | 7/2000 | Goble et al. |
| 6,112,123 A | 8/2000 | Kelleher et al. |
| 6,119,041 A | 9/2000 | Pomeranz et al. |
| 6,139,570 A | 10/2000 | Saadat et al. |
| 6,139,571 A | 10/2000 | Fuller et al. |
| 6,179,803 B1 | 1/2001 | Edwards et al. |
| 6,208,881 B1 | 3/2001 | Champeau |
| 6,233,490 B1 | 5/2001 | Kasevich |
| 6,238,393 B1 | 5/2001 | Mulier et al. |
| 6,272,370 B1 | 8/2001 | Gillies et al. |
| 6,302,904 B1 | 10/2001 | Wallsten et al. |
| 6,315,777 B1 | 11/2001 | Comben |
| 6,328,735 B1 * | 12/2001 | Curley .......... A61B 18/04 606/14 |
| 6,337,994 B1 | 1/2002 | Stoianovici et al. |
| 6,358,273 B1 | 3/2002 | Strul et al. |
| 6,405,067 B1 | 6/2002 | Mest et al. |
| 6,409,722 B1 | 6/2002 | Hoey et al. |
| 6,411,852 B1 | 6/2002 | Danek et al. |
| 6,443,947 B1 | 9/2002 | Marko et al. |
| 6,463,332 B1 | 10/2002 | Aldrich |
| 6,464,694 B1 | 10/2002 | Massengill |
| 6,468,274 B1 | 10/2002 | Alleyne et al. |
| 6,475,213 B1 | 11/2002 | Whayne et al. |
| 6,477,396 B1 | 11/2002 | Mest et al. |
| 6,494,902 B2 | 12/2002 | Hoey et al. |
| 6,529,756 B1 | 3/2003 | Phan et al. |
| 6,564,096 B2 | 5/2003 | Mest |
| 6,565,561 B1 | 5/2003 | Goble et al. |
| 6,603,997 B2 | 8/2003 | Doody |
| 6,620,155 B2 | 9/2003 | Underwood et al. |
| 6,641,580 B1 | 11/2003 | Edwards et al. |
| 6,669,685 B1 | 12/2003 | Rizoiu et al. |
| 6,678,552 B2 | 1/2004 | Pearlman |
| 6,702,810 B2 | 3/2004 | McClurken et al. |
| 6,752,802 B1 | 6/2004 | Isenberg et al. |
| 6,772,012 B2 | 8/2004 | Ricart et al. |
| 6,814,730 B2 | 11/2004 | Li |
| 6,904,303 B2 | 6/2005 | Phan et al. |
| 6,972,014 B2 | 12/2005 | Eum et al. |
| 7,001,378 B2 | 2/2006 | Yon et al. |
| 7,070,597 B2 | 7/2006 | Truckai et al. |
| 7,101,369 B2 | 9/2006 | van der Welde |
| 7,160,259 B2 | 1/2007 | Tardy et al. |
| 7,179,256 B2 | 2/2007 | Mest |
| 7,207,989 B2 | 4/2007 | Pike, Jr. et al. |
| 7,244,254 B2 | 7/2007 | Brace et al. |
| 7,270,659 B2 | 9/2007 | Ricart et al. |
| 7,311,703 B2 | 12/2007 | Turovskiy et al. |
| 7,387,625 B2 | 6/2008 | Hovda et al. |
| 7,387,630 B2 | 6/2008 | Mest |
| 7,412,273 B2 | 8/2008 | Jais et al. |
| 7,416,552 B2 | 8/2008 | Paul et al. |
| 7,559,905 B2 | 7/2009 | Kagosaki et al. |
| 7,604,634 B2 | 10/2009 | Hooven |
| 7,879,030 B2 | 2/2011 | Paul et al. |
| 7,938,822 B1 | 5/2011 | Berzak et al. |
| 7,951,143 B2 | 5/2011 | Wang et al. |
| 7,993,335 B2 | 8/2011 | Rioux et al. |
| 8,128,620 B2 | 3/2012 | Wang et al. |
| 8,128,621 B2 | 3/2012 | Wang et al. |
| 8,273,082 B2 | 9/2012 | Wang et al. |
| 8,287,531 B2 | 10/2012 | Mest |
| 8,333,762 B2 | 12/2012 | Mest et al. |
| 8,369,922 B2 | 2/2013 | Paul et al. |
| 8,439,907 B2 | 5/2013 | Auth et al. |
| 8,444,638 B2 | 5/2013 | Woloszko et al. |
| 8,449,535 B2 | 5/2013 | Deno et al. |
| 8,515,560 B2 | 8/2013 | Debruyne et al. |
| 8,591,507 B2 | 11/2013 | Kramer et al. |
| 8,663,226 B2 | 3/2014 | Germain |
| 8,700,133 B2 | 4/2014 | Hann |
| 8,702,697 B2 | 4/2014 | Curley |
| 8,755,860 B2 | 6/2014 | Paul et al. |
| 8,758,349 B2 | 6/2014 | Germain et al. |
| 8,864,760 B2 | 10/2014 | Kramer et al. |
| 8,945,121 B2 | 2/2015 | Curley |
| 9,033,972 B2 | 5/2015 | Curley |
| 9,125,671 B2 | 9/2015 | Germain et al. |
| 9,138,287 B2 | 9/2015 | Curley et al. |
| 9,138,288 B2 | 9/2015 | Curley |
| 9,445,861 B2 | 9/2016 | Curley |
| 9,610,396 B2 | 4/2017 | Curley et al. |
| 9,730,748 B2 | 8/2017 | Curley |
| 9,743,984 B1 | 8/2017 | Curley et al. |
| 2001/0031946 A1 | 10/2001 | Walker et al. |
| 2002/0120259 A1 | 8/2002 | Lettice et al. |
| 2002/0123749 A1 | 9/2002 | Jain |
| 2002/0153046 A1 | 10/2002 | Dantsker et al. |
| 2002/0183735 A1 | 12/2002 | Edwards et al. |
| 2003/0109871 A1 | 6/2003 | Johnson et al. |
| 2003/0120271 A1 | 6/2003 | Burnside et al. |
| 2004/0006336 A1 | 1/2004 | Swanson |
| 2004/0116922 A1 * | 6/2004 | Hovda .......... A61B 18/148 606/41 |
| 2004/0220559 A1 | 11/2004 | Kramer et al. |

(56) References Cited

U.S. PATENT DOCUMENTS

| | | |
|---|---|---|
| 2004/0230190 A1 | 11/2004 | Dahla et al. |
| 2004/0260282 A1 | 12/2004 | Gough et al. |
| 2005/0015081 A1 | 1/2005 | Turovskiy et al. |
| 2005/0055019 A1 | 3/2005 | Skarda |
| 2005/0059963 A1 | 3/2005 | Phan et al. |
| 2005/0165391 A1 | 7/2005 | Maguire et al. |
| 2005/0187599 A1 | 8/2005 | Sharkey et al. |
| 2005/0192652 A1 | 9/2005 | Cioanta et al. |
| 2005/0245923 A1 | 11/2005 | Christopherson et al. |
| 2005/0267552 A1 | 12/2005 | Conquergood et al. |
| 2006/0085054 A1 | 4/2006 | Zikorus et al. |
| 2006/0118127 A1 | 6/2006 | Chinn |
| 2006/0129091 A1 | 6/2006 | Bonnette et al. |
| 2006/0216275 A1 | 9/2006 | Mon |
| 2006/0259024 A1 | 11/2006 | Turovskiy et al. |
| 2006/0276780 A1 | 12/2006 | Brace et al. |
| 2006/0287650 A1 | 12/2006 | Cao et al. |
| 2007/0027448 A1 | 2/2007 | Paul et al. |
| 2007/0032786 A1 | 2/2007 | Francischelli |
| 2007/0167775 A1 | 7/2007 | Kochavi et al. |
| 2007/0185483 A1 | 8/2007 | Butty et al. |
| 2007/0219434 A1 | 9/2007 | Abreu |
| 2007/0287998 A1 | 12/2007 | Sharareh et al. |
| 2007/0288075 A1 | 12/2007 | Dowlatshahi |
| 2008/0086073 A1 | 4/2008 | McDaniel |
| 2008/0154258 A1 | 6/2008 | Chang et al. |
| 2008/0161788 A1 | 7/2008 | Dando et al. |
| 2008/0161797 A1 | 7/2008 | Wang et al. |
| 2008/0167650 A1 | 7/2008 | Joshi et al. |
| 2008/0275438 A1 | 11/2008 | Gadsby et al. |
| 2008/0275440 A1 | 11/2008 | Kratoska et al. |
| 2008/0288038 A1 | 11/2008 | Paul et al. |
| 2009/0069808 A1 | 3/2009 | Pike, Jr. et al. |
| 2009/0082837 A1 | 3/2009 | Gellman et al. |
| 2009/0093811 A1 | 4/2009 | Koblish et al. |
| 2009/0118725 A1 | 5/2009 | Auth et al. |
| 2009/0118727 A1 | 5/2009 | Pearson et al. |
| 2009/0163836 A1 | 6/2009 | Sliwa |
| 2009/0192507 A1 | 7/2009 | Luttich |
| 2009/0254083 A1 | 10/2009 | Wallace et al. |
| 2010/0030098 A1 | 2/2010 | Fojtik |
| 2010/0094272 A1 | 4/2010 | Rossetto et al. |
| 2010/0198056 A1 | 8/2010 | Fabro et al. |
| 2010/0292766 A1 | 11/2010 | Duong et al. |
| 2010/0324471 A1 | 12/2010 | Flaherty et al. |
| 2011/0060349 A1 | 3/2011 | Cheng et al. |
| 2011/0137150 A1 | 6/2011 | Connor et al. |
| 2011/0160726 A1 | 6/2011 | Ingle |
| 2011/0184403 A1 | 7/2011 | Brannan |
| 2011/0190756 A1 | 8/2011 | Venkatachalam et al. |
| 2011/0230799 A1 | 9/2011 | Christian et al. |
| 2011/0251615 A1 | 10/2011 | Truckai et al. |
| 2011/0270246 A1 | 11/2011 | Clark et al. |
| 2012/0108938 A1 | 5/2012 | Kauphusman et al. |
| 2012/0130381 A1 | 5/2012 | Germain |
| 2012/0165812 A1 | 6/2012 | Christian |
| 2012/0265190 A1 | 10/2012 | Curley et al. |
| 2012/0265199 A1 | 10/2012 | Curley |
| 2012/0265200 A1 | 10/2012 | Curley |
| 2012/0265276 A1 | 10/2012 | Curley |
| 2012/0277737 A1 | 11/2012 | Curley |
| 2012/0310230 A1 | 12/2012 | Willis |
| 2014/0052117 A1 | 2/2014 | Curley |
| 2014/0058386 A1 | 2/2014 | Clark et al. |
| 2014/0188106 A1 | 7/2014 | Curley |
| 2014/0275977 A1 | 9/2014 | Curley et al. |
| 2014/0276743 A1 | 9/2014 | Curley |
| 2014/0350542 A1 | 11/2014 | Kramer et al. |
| 2015/0066025 A1 | 3/2015 | Curley |
| 2015/0223882 A1 | 8/2015 | Curley |
| 2015/0351823 A1 | 12/2015 | Curley |
| 2015/0359582 A1 | 12/2015 | Curley et al. |
| 2017/0238993 A1 | 8/2017 | Curley |

FOREIGN PATENT DOCUMENTS

| | | |
|---|---|---|
| CN | 1525839 A | 9/2004 |
| CN | 1897885 A | 1/2007 |
| CN | 101209217 A | 7/2008 |
| CN | 101578073 A | 11/2009 |
| CN | 101773699 A | 7/2010 |
| CN | 201642316 U | 11/2010 |
| CN | 101999931 A | 4/2011 |
| EP | 0 895 756 A1 | 2/1999 |
| EP | 2 042 112 A2 | 4/2009 |
| EP | 2 430 996 A2 | 3/2012 |
| JP | 10-505268 A | 5/1998 |
| WO | 96/07360 A1 | 3/1996 |
| WO | 96/34569 A1 | 11/1996 |
| WO | 96/36288 A1 | 11/1996 |
| WO | 97/29702 A1 | 8/1997 |
| WO | 98/29068 A1 | 7/1998 |
| WO | 99/32186 A1 | 7/1999 |
| WO | 02/089686 A1 | 11/2002 |
| WO | 2005/048858 A1 | 6/2005 |
| WO | 2005/089663 A1 | 9/2005 |
| WO | 2006/055658 A1 | 5/2006 |
| WO | 2006/095171 A1 | 9/2006 |
| WO | 2006/102471 A2 | 9/2006 |
| WO | 2006/103951 A1 | 10/2006 |
| WO | 2007/080578 A2 | 7/2007 |
| WO | 2010/002733 A1 | 1/2010 |
| WO | 2010/151619 A2 | 12/2010 |
| WO | 2012/071058 A1 | 5/2012 |

OTHER PUBLICATIONS

Brace CL. Microwave tissue ablation: biophysics, technology, and applications.; Crit Rev Biomed Eng. 2010;38(1):65-78.
Chinese Office Action for Application No. 201280028609.9, dated May 27, 2015. (22 pages).
Chinese Office Action for Application No. 201280028611.6, dated Jul. 29, 2015. (23 pages).
Chinese Office Action for Application No. 201280028620.5, dated May 27, 2015. (26 pages).
Chinese Office Action for Application No. 201280028621.X, dated Jul. 31, 2015. (18 pages).
Extended Search Report and Written Opinion for EP 12770537.4 dated Oct. 10, 2014 (6 pages).
Extended Search Report and Written Opinion for EP 12770631.5 dated Oct. 1, 2014 (6 Pages).
Extended Search Report and Written Opinion for EP 12771331.1 dated Sep. 25, 2014 (6 Pages).
Extended European Search Report and Written Opinion for Application No. 12771601.7 dated Oct. 27, 2014 (7 pages).
Extended Search Report and Written Opinion for EP 12 77 1876 dated Oct. 13, 2014 (6 pages).
Extended European Search Report and Search Opinion for Application No. 13829821.1 dated Mar. 17, 2016 (7 pages).
International Search Report and Written Opinion for Application No. PCT/US2012/033203, dated Sep. 21, 2012. (23 pages).
International Search Report and Written Opinion for Application No. PCT/US2012/033213, dated Sep. 21, 2012. (17 pages).
International Search Report and Written Opinion for Application No. PCT/US2012/033216, dated Sep. 21, 2012. (17 pages).
International Search Report and Written Opinion for Application No. PCT/US2012/033327, dated Sep. 21, 2012. (14 pages).
International Search Report and Written Opinion for Application No. PCT/US2012/033332, dated Sep. 21, 2012. (20 pages).
International Search Report and Written Opinion for Application No. PCT/US2013/053977, dated Nov. 14, 2013. (20 pages).
International Search Report and Written Opinion for Application No. PCT/US2014/024731, dated Jul. 21, 2014 (39 pages).
Japanese Office Action for Application No. 2014-505263, dated Jan. 26, 2016 (4 pages).
Japanese Office Action for Application No. 2014-505266, dated Feb. 23, 2016 (7 pages).

(56) References Cited

OTHER PUBLICATIONS

David R. Lide (ed.), CRC Handbook of Chemistry and Physics, 87th Edition. 2006. p. 8-81. CRC Press, Florida.
Nath et al., Prog. Card. Dis. 37(4):185-205 (1995).
Rolf Sander, Compilation of Henry's Law Constants for Inorganic and Organic Species of Potential Importance in Environmental Chemistry. Max-Planck Institute of Chemistry. 1999, Mainz Germany. Www.henrys-law.org.
Sapareto et al., Int. J Rad. One. Biol. Phys. 10(6):787-800 (1984).
Young, S.T., et al., An instrument using variation of resistance to aid in needle tip insertion in epidural block in monkeys. Med Instrum. Oct. 1987;21(5):266-8. Abstract Only.
U.S. Appl. No. 13/445,034, filed Apr. 12, 2012, Devices and Methods for Remote Temperature Monitoring in Fluid Enhanced Ablation Therapy.
U.S. Appl. No. 13/445,036, filed Apr. 12, 2012, Methods and Devices for Heating Fluid in Fluid Enhanced Ablation Therapy.
U.S. Appl. No. 13/445,040, filed Apr. 12, 2012, Methods and Devices for Use of Degassed Fluids With Fluid Enhanced Ablation Devices.
U.S. Appl. No. 13/445,365, filed Apr. 12, 2012, Devices and Methods for Shaping Therapy in Fluid Enhanced Ablation.
U.S. Appl. No. 13/445,373, filed Apr. 12, 2012, Methods and Devices for Controlling Ablation Therapy.
U.S. Appl. No. 13/586,559, filed Aug. 15, 2012, Low Profile Fluid Enhanced Ablation Therapy Devices and Methods.
U.S. Appl. No. 13/837,295, filed Mar. 15, 2013, Methods and Devices for Fluid Enhanced Microwave Ablation Therapy.
U.S. Appl. No. 13/842,561, filed Mar. 15, 2013, Systems and Methods for Visualizing Fluid Enhanced Ablation Therapy.
U.S. Appl. No. 14/202,425, filed Mar. 10, 2014, Devices and Methods for Shaping Therapy in Fluid Enhanced Ablation.
U.S. Appl. No. 14/536,212, filed Nov. 7, 2014, Methods and Devices for Use of Degassed Fluids With Fluid Enhanced Ablation Devices.
U.S. Appl. No. 14/688,790, filed Apr. 16, 2015, Methods and Devices for Fluid Enhanced Microwave Ablation Therapy.
U.S. Appl. No. 14/826,549, filed Aug. 14, 2015, Methods and Devices for Heating Fluid in Fluid Enhanced Ablation Therapy.
U.S. Appl. No. 14/826,563, filed Aug. 14, 2015, Methods and Devices for Use of Degassed Fluids With Fluid Enhanced Ablation Devices.
U.S. Appl. No. 15/234,858, filed Aug. 11, 2016, Devices and Methods for Delivering Fluid to Tissue During Ablation Therapy.
Chinese Office Action for Application No. 201280028612.0, dated Nov. 2, 2016. (8 pages).
Chinese Office Action for Application No. 201380053690.0, dated Jul. 20, 2017. (18 pages).
U.S. Appl. No. 15/450,806, filed Mar. 6, 2017, Devices and Methods for Remote Temperature Monitoring in Fluid Enhanced Ablation Therapy.
U.S. Appl. No. 15/476,371, filed Mar. 31, 2017, Systems and Methods for Visualizing Fluid Enhanced Ablation Therapy.
U.S. Appl. No. 15/663,914, filed Jul. 31, 2017, Devices and Methods for Shaping Therapy in Fluid Enhanced Ablation.
U.S. Appl. No. 15/663,929, filed Jul. 31, 2017, Devices and Methods for Delivering Fluid to Tissue During Ablation Therapy.

* cited by examiner

METHODS AND DEVICES FOR CONTROLLING ABLATION THERAPY

RELATED APPLICATIONS

This application is a divisional of U.S. application Ser. No. 13/445,373, filed on Apr. 12, 2012, now issued as U.S. Pat. No. 9,445,861 and entitled "Methods and Devices for Controlling Ablation Therapy," which claims priority to U.S. Provisional Application No. 61/474,574, filed on Apr. 12, 2011, entitled "Ablation Catheters." This application is also related to U.S. application Ser. No. 13/445,034, entitled "Devices and Methods for Remote Temperature Monitoring in Fluid Enhanced Ablation Therapy," U.S. application Ser. No. 13/445,036, now issued as U.S. Pat. No. 9,138,287 and entitled "Methods and Devices for Heating Fluid in Fluid Enhanced Ablation Therapy," U.S. application Ser. No. 13/445,040, now issued as U.S. Pat. No. 8,945,121 and entitled "Methods and Devices for Use of Degassed Fluids with Fluid Enhanced Ablation Devices," and U.S. application Ser. No. 13/445,365, now issued as U.S. Pat. No. 8,702,697 and entitled "Devices and Methods for Shaping Therapy in Fluid Enhanced Ablation," all of which were filed concurrently with the present application. The disclosures of each of these applications are hereby incorporated by reference in their entirety.

FIELD

The present application relates generally to the control of ablation therapy. More particularly, this application relates to improved devices and methods for controlling ablation therapy.

BACKGROUND

The use of thermal energy to destroy bodily tissue can be applied to a variety of therapeutic procedures, including the treatment of cardiac arrhythmias, such as atrial fibrillation. In such a procedure, thermal energy can be imparted to the arrhythmogenic myocardium using various forms of energy, such as radio frequency electrical energy, microwave or light wave electromagnetic energy, or ultrasonic vibrational energy. Radio frequency (RF) ablation, for example, can be effected by placing a catheter within the heart and pressing an emitting electrode disposed on the catheter against the heart wall near the region of the myocardium that is causing the arrhythmia. High frequency electrical current can be passed into the tissue between closely spaced emitting electrodes or between the emitting electrode and a larger, common electrode located remotely from the tissue to be heated. The energy can heat the myocardium to a temperature that will cause necrosis (e.g., a temperature above about 50° C.).

One embodiment of a prior art ablation catheter is shown in FIG. 1. The catheter 100 includes a plurality of sensing electrodes 102 disposed thereon that are used to detect electrical activity in the heart. The measurement of electrical activity can be used to detect the arrhythmogenic tissue and guide the placement of the catheter. The catheter also includes a large electrode or other ablation element 104 disposed on the distal end thereof that is effective to transmit RF electrical energy into the myocardium 106. In use, the electrode 104 on the distal tip of the catheter 100 is placed against the surface of the myocardium 106 in a desired location, and the electrode is subsequently activated to heat the tissue.

Prior art ablation catheters have a number of disadvantages. For example, using the above techniques, maximum heating often occurs at or near the interface between the catheter electrode 104 and the tissue 106. In RF ablation, for example, maximum heating can occur in the tissue immediately adjacent to the emitting electrode. Furthermore, as these techniques are increasingly used in areas having thicker tissue walls, the RF power level must be increased to effect heating at greater depths within the tissue. This can result in even higher levels of heating at the interface between the electrode and the tissue. As described in more detail below, these high levels of heating can reduce the conductivity of the tissue, effectively preventing the transmission of further energy into the tissue. In addition, some levels of heating can produce dangerous medical complications for a patient, including, for example, clots that can result from overheating surrounding blood.

Accordingly, there is a need for improved methods and devices for controlling ablation therapy.

SUMMARY

The present invention generally provides devices and methods for controlling ablation therapy. In particular, the devices and methods described herein permit regulation of the temperature of an ablation element being used to emit ablative energy into tissue. By controlling the temperature of the ablation element, the undesirable effects associated with overheating the tissue can be avoided. This, in turn, can allow a greater amount of tissue to be treated using a lower amount of ablative energy, thereby reducing the risk of unintended damage to tissue.

In one aspect, an ablation device is provided that includes an elongate body having proximal and distal ends, and an inner lumen extending therethrough. The device further includes an ablation element positioned at the distal end of the elongate body, the ablation element being configured to heat surrounding tissue. The inner lumen of the elongate body is configured to receive fluid therein such that the fluid flows to the distal end of the elongate body. The device further includes a heater element disposed within the inner lumen adjacent to a distal end thereof. The heater element can be configured to heat fluid flowing through the inner lumen.

The devices and methods described herein can have a variety of modifications and additional features, all of which are considered within the scope of the invention. For example, in some embodiments the elongate body and the ablation element can be non-porous such that fluid is preventing from flowing therethrough. The inner lumen can include a delivery lumen, as well as a return lumen such that fluid can flow distally through the delivery lumen to the distal end, and then flow proximally through the return lumen to the proximal end of the elongate body. In other embodiments, the elongate body can include one or more outlet ports formed through a sidewall thereof adjacent to the distal end thereof, the outlet ports being configured to allow fluid to flow from the inner lumen and into surrounding tissue.

In certain embodiments, the device can further include a temperature sensor disposed on a distal end of the ablation element to sample a temperature at the interface between the ablation element and a tissue wall. In certain embodiments, the temperature sensor can be recessed within the ablation element such that it does not protrude from a distal end thereof. In other embodiments still, the temperature sensor can be disposed within the inner lumen of the elongate body and in contact with the ablation element.

In some embodiments, the device can include a different temperature sensor positioned adjacent to the distal end of the inner lumen at a location distal to the heater element in order to sample a temperature of fluid heated by the heater element. Still further, in some embodiments the device can include a temperature sensor positioned proximal to the heater element within the inner lumen to sample the temperature of fluid flowing through the inner lumen.

The heater element can have a variety of forms. In some embodiments, the heater element can include at least one wire extending through the inner lumen and configured to pass Radio Frequency (RF) electrical energy through fluid flowing through the inner lumen. In other embodiments, the heater element can be a resistive element disposed within the inner lumen.

The ablation element can, in some embodiments, form a blunt distal tip of the elongate body that is configured to contact tissue without penetrating through the tissue. In other embodiments, however, the ablation element can have a variety of other shapes.

In another aspect, a method of ablating tissue is provided that includes positioning a blunt distal portion of an elongate body in contact with tissue, and delivering ablative energy to the tissue through an ablation element while simultaneously delivering fluid through the elongate body where the fluid is heated by a heater element disposed in a distal portion of the elongate body. The fluid can be heated to control the ablation therapy provided to the tissue by the ablation element.

In some embodiments, the blunt distal portion of the elongate body does not penetrate the tissue when positioned in contact therewith, but rather abuts against a surface of the tissue. In other embodiments, the ablation element is positioned at that distal end of the elongate body, such that the distal end of the elongate body is positioned in contact with tissue.

In other embodiments, delivering fluid through the elongate body can include forcing fluid through an inner lumen disposed within the elongate body. In certain embodiments, the heater element can be disposed within the inner lumen. In still other embodiments, the method can further include receiving fluid delivered through the elongate body at a proximal end thereof, e.g., such that the fluid circulates through the elongate body without exiting at the distal end of the elongate body. In some embodiments, however, the fluid delivered through the elongate body can flow through one or more outlet ports formed in the ablation element into the surrounding tissue or fluid.

In certain embodiments, the method can further include detecting a temperature of the tissue in contact with the blunt distal portion of the elongate body using a temperature sensor disposed on a distal end of the elongate body. In other embodiments, however, the method can include detecting the temperature of the fluid delivered through the elongate body using a temperature sensor disposed distal to the heater element.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. The terms "about" and "approximately" used for any numerical values or ranges indicate a suitable dimensional tolerance that allows the composition, part, or collection of elements to function for its intended purpose as described herein. These terms generally indicate a ±10% variation about a central value. Components described herein as being coupled may be directly coupled, or they may be indirectly coupled via one or more intermediate components. The recitation of any ranges of values herein is merely intended to serve as a shorthand method of referring individually to each separate value falling within the range, unless otherwise indicated herein, and each separate value is incorporated into the specification as if it were individually recited. All methods described herein can be performed in any suitable order unless otherwise indicated herein or otherwise clearly contradicted by context. The use of any and all examples, or exemplary language (e.g., "such as"), provided herein is intended merely to better illuminate the invention and does not impose a limitation on the scope of the invention unless otherwise claimed. No language in the specification should be construed as indicating any non-claimed element as essential to the practice of the invention. Further, to the extent the term "saline" is used in conjunction with any embodiment herein, such embodiment is not limited to the use of "saline" as opposed to another fluid unless explicitly indicated. Other fluids can typically be used in a similar manner.

Figure 1:
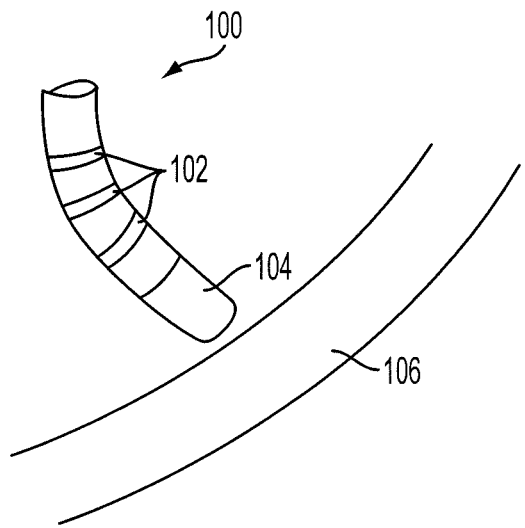
FIG. 1 is a diagram of one embodiment of a prior art ablation device.
Figure 2:
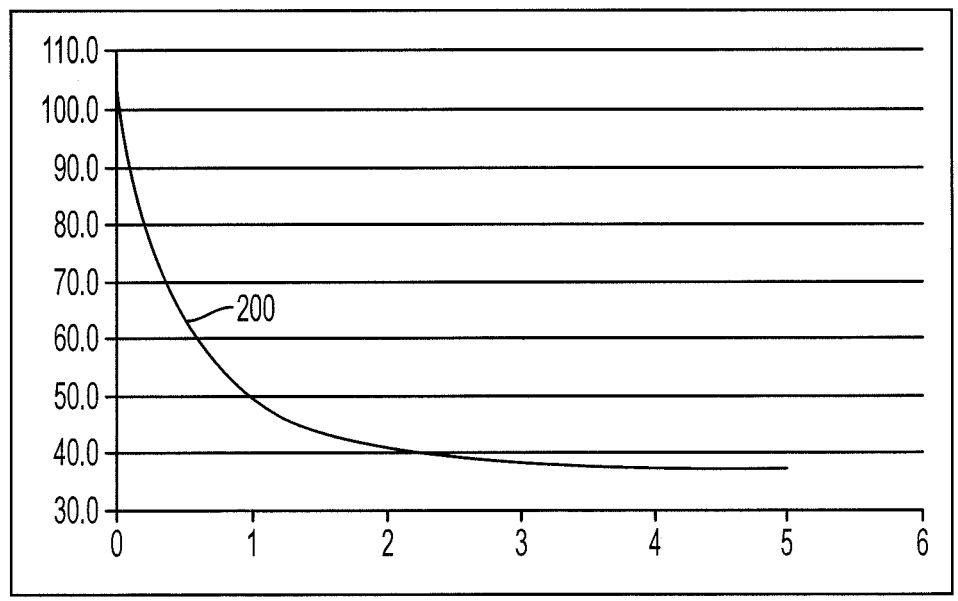
FIG. 2 is a chart showing a temperature profile created in tissue by the prior art ablation device of FIG. 1.

As described above, conventional ablation techniques using a device similar to the ablation catheter 100 of FIG. 1 can produce maximal heating of tissue at the interface between the ablation element, such as electrode 104, and the tissue, such as myocardium 106. Use of such a device can produce the temperature profile 200 of FIG. 2 that illustrates the temperature (in degrees Celsius) as a function of the depth (in millimeters) from the tissue surface. As shown in the figure, the ablation catheter 100 can create a therapeutically treated lesion in tissue that is 1 mm deep. That is, the depth to which the tissue is heated above 50° C. is 1 mm. A temperature of 50° C. is used herein as an example of a threshold for determining when a particular volume of tissue has been therapeutically treated, i.e., has received a thermal dose sufficient to cause necrosis within the volume (see Nath, S. and Haines, D. E., *Prog. Card. Dis.* 37(4):185-205 (1995) (Nath et al.)). However, this number is provided by way of example only, as the literature contains a number of different methodologies for determining thermal dose administration, any of which can be utilized with the methods and devices of the present invention.

Referring back to FIG. 2, the shallow treatment depth produced by the prior art ablation catheter 100 is often only effective for use with superficial arrhythmogenic tissue or, for example, in regions of the heart where the wall is very thin (e.g., thin atrial walls). As the use of ablation in the treatment of atrial fibrillation and other cardiac conditions has increased over time, ablation therapy has been used in areas having much thicker tissue walls. One method for increasing the depth to which an ablation catheter can heat is to cool the surface of the ablation element, e.g., the electrode 104. To accomplish this, a fluid can be pumped down the ablation catheter to contact the ablation element disposed adjacent to the distal end of the catheter. In some cases, the fluid can contact a rear surface of the ablation element and return up the catheter body. In other cases, however, the fluid can flow out of the ablation catheter through one or more ports or pores formed in the ablation element itself.

In either case, fluid (e.g., saline) can be introduced into the ablation catheter at room temperature and is often heated to near body temperature by the surrounding blood as the fluid moves through the body toward the distal end of the catheter. The flowing body-temperature fluid can cool and constrain the ablation element to a temperature that is about body temperature, or 37° C.

Figure 3:
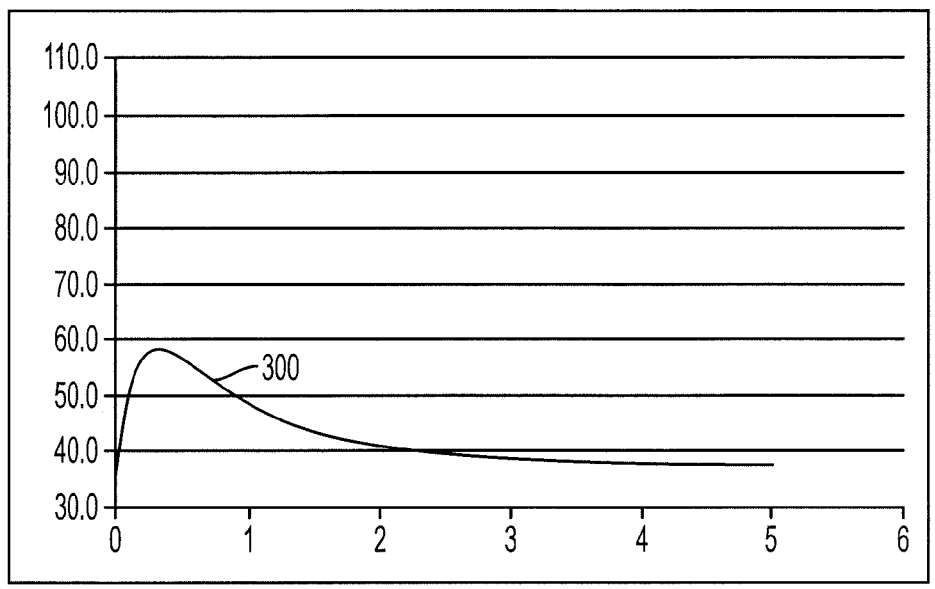
FIG. 3 is a chart showing a temperature profile created in tissue by a prior art ablation device cooled by unheated fluid.

An exemplary temperature profile created by such a device is shown in FIG. 3. As the profile 300 illustrates, contacting the ablation element with body-temperature fluid can be effective to reduce the heating that occurs at the interface between the ablation element and the tissue wall. However, the cooling can also be effective to reduce the entire heating field to such a degree that the effectiveness of the ablation therapy is reduced, i.e., only a very small portion of tissue is heated above the desired therapeutic temperature of 50° C. This same effect can also be seen in areas of the heart (or other organs) where blood vessels or arteries produce effective localized cooling by moving blood past the treatment site. For example, in atrial fibrillation it can be necessary to perform ablation near the coronary sinus, and the large amount of blood flow in this area can effectively cool the heating fields created by any ablation devices.

Figure 4:
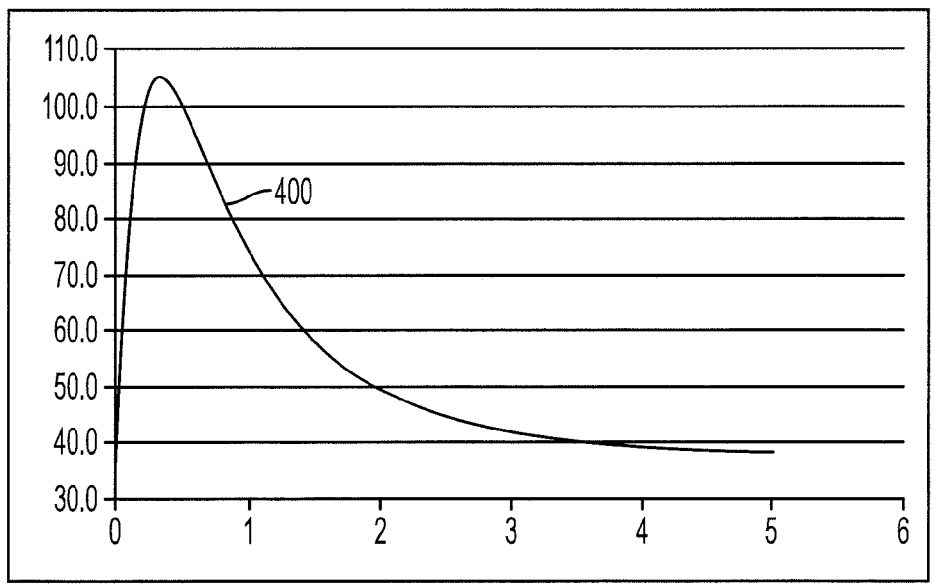
FIG. 4 is a chart showing a temperature profile created in tissue by the device of FIG. 3 following an increase in ablative energy level.

To compensate for this cooling effect, the level of RF power used to heat the tissue can be increased. An increase in RF power in combination with fluid cooling of the ablation element can, for example, produce the temperature profile 400 shown in FIG. 4. The increase in power can have the positive effect of increasing the depth of therapeutic treatment (e.g., the depth of therapeutic treatment increases to 2 mm), but comes at the cost of producing a higher maximum temperature within the tissue. Furthermore, the position of the maximum temperature can be shifted into the tissue as a result of the cooling of the ablation element. Because this maximum temperature can no longer be directly observed due to its position at depth, it can be difficult to control the balance between the amount of RF heating and the amount of cooling provided by the fluid. In such a situation, temperatures within the tissue can exceed 100° C. in some locations, as shown in FIG. 4. Exceeding 100° C. can produce a number of undesirable effects. For example, above 100° C. tissue can desiccate, or dry up, and overheat. This can produce charring and lead to an increase in the impedance of the tissue. As the impedance increases, the amount of electrical energy that can pass through the tissue decreases. Accordingly, impedance rises can effectively stop any further ablation therapy since energy is no longer transferred deeper into the tissue. Still further, such high temperatures can also cause superheating of any fluid in the tissue. In some cases, impedance pops—or the explosive phase change of superheated fluid to steam—can occur. These small explosions can cause damage in the tissue wall and potentially lead to serious medical complications (e.g., perforations in the heart wall, etc.).

Figure 5:
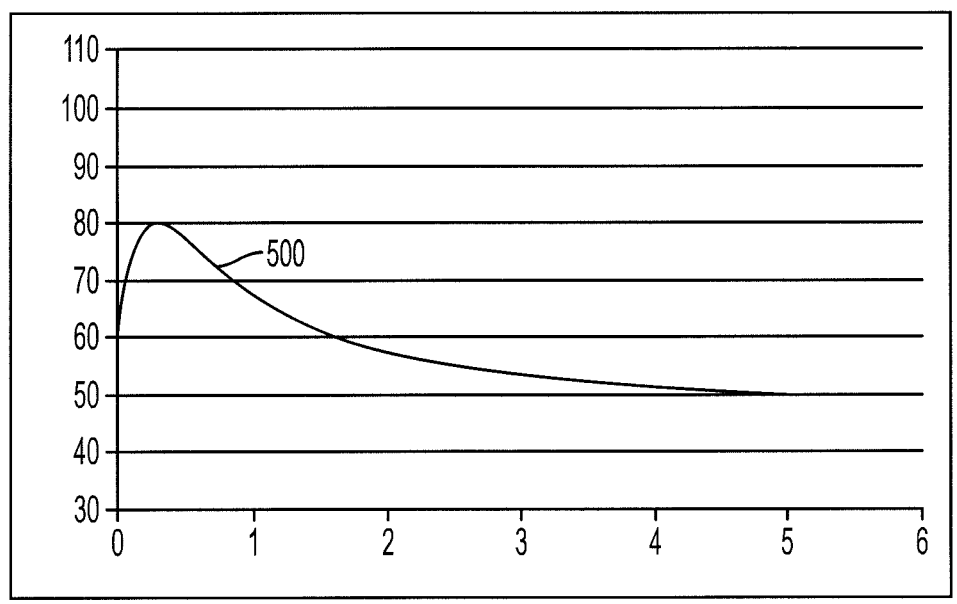
FIG. 5 is a chart showing a temperature profile created in tissue using one embodiment of an ablation device of the present invention.

To address these issues, methods and devices are provided herein to control the temperature and power level of an ablation element to thereby prevent undesirable temperature spikes while maintaining the depth of the treatment lesion created during ablation therapy. FIG. 5 illustrates an exemplary temperature profile 500 that can be achieved using the methods and devices described herein. In one embodiment, a heating element can be implemented in an ablation device to deliver fluid at a controlled and desired temperature to cool an ablation element. The temperature of the fluid can be selected such that the ablation element is cooled to a temperature below about 100° C. More preferably, the fluid can be cooled to a temperature between about 20° C. and 100° C. Still more preferably, the fluid can be cooled to a temperature between about 37° C. and 100° C.

For example, and as shown in the figure, the ablation element can be cooled to a temperature of about 60° C. Regulating the temperature of the ablation element to this level can prevent the desiccation and impedance rise associated with heating above 100° C., but can also allow for deeper therapeutic heating using a lower RF power level. For example, the profile 500 shows that tissue to a depth of 5 mm can be heated above 50° C. with no tissue rising above about 80° C. While 60° C. is illustrated as an example, any temperature between about 37° C. and 100° C. can be selected. For example, a temperature of 40, 50, 60, 70, 80, or 90° C. can be selected. The selection of the fluid temperature (which can approximate the ablation element temperature because the flowing fluid can cool the ablation element to approximately the same temperature) and RF power level can be coordinated such that a treatment lesion of a desired depth is created without heating any portion of the tissue above about 100° C.

Figure 6:
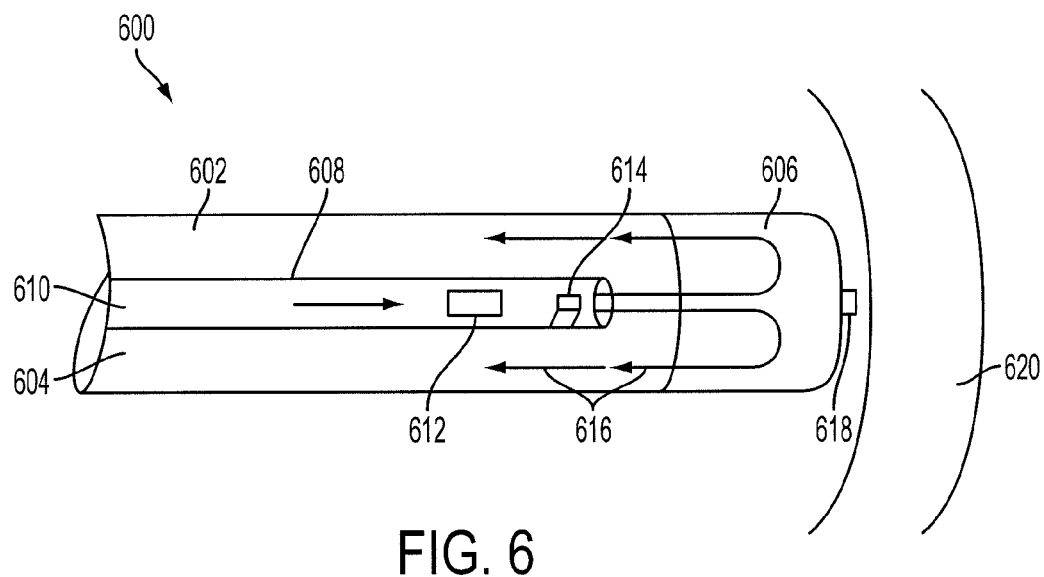
FIG. 6 is a side view of one embodiment of an ablation device having a closed loop flow pattern.

A number of different devices and methods can be employed to heat the cooling fluid to a desired temperature. FIG. 6 illustrates one embodiment of an ablation device 600. The device 600 includes an elongate body, which can be rigid or flexible and can be formed from a variety of biocompatible materials. For example, the elongate body 602 can be a flexible catheter body, or can be a rigid body disposed at a distal end of a catheter used to introduce the elongate body 602 to a treatment site. The elongate body 602 can also include an inner lumen 604 extending therethrough that can be configured to provide a passage for fluid flow through the elongate body. Further, the particular size of the elongate body can depend on a variety of factors including the type and location of tissue to be treated, etc. By way of example only, in one embodiment, a very small elongate body can be utilized to access the heart of a patient. In such an embodiment, an appropriately sized elongate body can be, for example, a catheter having a diameter of about 8 French ("French" is a unit of measure used in the catheter industry to describe the size of a catheter and is equal to three times the diameter of the catheter in millimeters). The elongate body can be formed from a conductive material such that the elongate body can conduct electrical energy along its length to an ablation element disposed thereon. Alternatively, the elongate body can be formed from, or coated in, an insulating material and any electrical communication between any components coupled thereto can be accomplished through electrical connections running along or within the elongate body.

The elongate body 602 can also include an ablation element 606 disposed along a length thereof adjacent to its distal end. As shown in the figure, in some embodiments the ablation element 606 can be positioned at the distal end of the elongate body 602. The ablation element 606 can be formed from a variety of materials suitable for conducting current. Any metal or metal salt may be used. Aside from stainless steel, exemplary metals include platinum, gold, or silver, and exemplary metal salts include silver/silver chloride. In one embodiment, the electrode can be formed from silver/silver chloride. It is known that metal electrodes assume a voltage potential different from that of surrounding tissue and/or liquid. Passing a current through this voltage difference can result in energy dissipation at the electrode/tissue interface, which can exacerbate excessive heating of the tissue near the electrodes. One advantage of using a metal salt such as silver/silver chloride is that it has a high exchange current density. As a result, a large amount of current can be passed through such an electrode into tissue with only a small voltage drop, thereby minimizing energy dissipation at this interface. Thus, an electrode formed from a metal salt such as silver/silver chloride can reduce excessive energy generation at the tissue interface and thereby produce a more desirable therapeutic temperature profile, even where there is no liquid flow about the electrode.

In some embodiments, the ablation element 606 can be disposed at a distal end of the elongate body 602. The ablation element 606 can have a variety of shapes but, in some embodiments, can be shaped to form a blunt distal tip of the device 600. As such, the ablation element 606 can be configured to press against, or be positioned adjacent to, a tissue wall without penetrating into the tissue wall. Furthermore, the ablation element 606 can be formed from a non-porous material or, in some embodiments, the ablation element 606 can have one or more outlet ports or pores formed therein that provide fluid communication between the inner lumen and the tissue and/or fluids surrounding the ablation element.

In some embodiments, the inner lumen of the elongate body 602 can include a delivery lumen 608 configured to provide a passage for fluid flow from the proximal end to the distal end, and a return lumen formed by the annular space between the delivery lumen 608 and the inner wall of the inner lumen 604. The return lumen can be configured to receive fluid at a distal end thereof and deliver the fluid back to the proximal end of the elongate body 602. This allows fluid to be circulated through the elongate body without the need to release the fluid to the surrounding tissue. Similar to the elongate body 602, the delivery lumen 608 can be formed from a variety of materials that are rigid, flexible, polymeric, metallic, conductive, or insulating. Further, the delivery lumen 608 can be positioned within the inner lumen 604 of the elongate body 602 such that the delivery lumen does not move with respect to the elongate body, or can be allowed to float freely within the elongate body 602. In some embodiments, the delivery lumen 608 can be a hollow tube disposed within the inner lumen of the elongate body. In addition, in certain embodiments, the return lumen can be a separate hollow tube disposed within the inner lumen 604 of the elongate body.

In some embodiments, the delivery lumen 608 can house a heating assembly or heater element 612 disposed adjacent to a distal end of the delivery lumen and configured to heat fluid flowing through the delivery lumen. The heating assembly 612 can be connected to a power supply and controller coupled to the proximal end of the elongate body 602. A number of heating assemblies can be utilized to heat fluid flowing through the delivery lumen 608, including those described in U.S. Pat. No. 6,328,735 to Curley et al., and U.S. patent application Ser. No. 13/445,036, entitled "Methods and Devices for Heating Fluid in Fluid Enhanced Ablation Therapy," filed concurrently herewith. The disclosures of each of these references are hereby incorporated by reference in their entirety. For example, the heater element 612 can be a resistive coil disposed within the delivery lumen 608. In other embodiments, however, a heating assembly 612 formed from one or more wires suspended in the delivery lumen 608 that can be used to pass RF electrical energy through the fluid flowing through the delivery lumen, thereby heating the fluid due to its inherent electrical resistivity.

In certain embodiments, the delivery lumen 608 can also house a temperature sensor 614 configured to detect the temperature of the fluid flowing through the delivery lumen 608 after it is heated by the heating assembly 612. For this reason, the temperature sensor 614 can, in some embodiments, be positioned distal to the heating assembly 612, and can be separated from the heating assembly by a distance sufficient to allow mixing of the fluid after passing through the heating assembly (e.g., about 1 mm). The temperature sensor 614 can have a variety of forms and, in some embodiments, can be a fine-wire thermocouple. The temperature sensor 614 can be connected to a controller that can utilize the detected fluid temperature to regulate the heating assembly 612.

In use, a fluid (e.g., saline) can be pumped through the delivery lumen 608 from a proximal end thereof to a distal end that is positioned adjacent to the ablation element 606. The fluid can pass by the heating assembly 612 and be heated to a desired temperature, e.g., any temperature below 100° C., or any temperature between about 40 and about 90° C., or between about 50 and about 80° C., or between about 60 and about 70° C. In some embodiments, an additional temperature sensor (not shown) can be positioned in the delivery lumen 608 at a position proximal to the heating assembly 612 in order to determine the initial temperature of the fluid flowing through the delivery lumen 608 (and thereby determine a power output needed for the heating assembly 612). After being heated by the heating assembly 612, the fluid can mix and exit the delivery lumen 608 near the distal end of the elongate body 602 adjacent to the ablation element 606. As shown by the flow direction arrows 616, the fluid can contact an inner surface of the ablation element and subsequently be directed back toward the proximal end of the elongate body 602 through the return lumen. The movement of the fluid can convect heat away from the ablation element 606, thereby regulating its temperature. Given a sufficient flow rate, the ablation element 606 can be regulated to about the same temperature of the fluid exiting the delivery lumen 608.

In order to confirm the effectiveness of the temperature regulation, the device 600 can also include an external temperature sensor 618 disposed on a distal end of the device 600. In some embodiments, the temperature sensor 618 can be recessed within the ablation element 606 such that it does not protrude from a distal end thereof. In still other embodiments in which the ablation element 606 is formed from a metal or other thermally conductive material, the temperature sensor 618 can be positioned inside the inner lumen 604 touching a proximal surface of the ablation element 606. Regardless of its position, the temperature sensor 618 can be configured to detect the temperature at the interface between the ablation element 606 and a tissue surface 620. Detecting the temperature at this location can confirm that the ablation element 606 is being cooled to the temperature of the fluid flowing from the delivery lumen 608.

Figure 7:
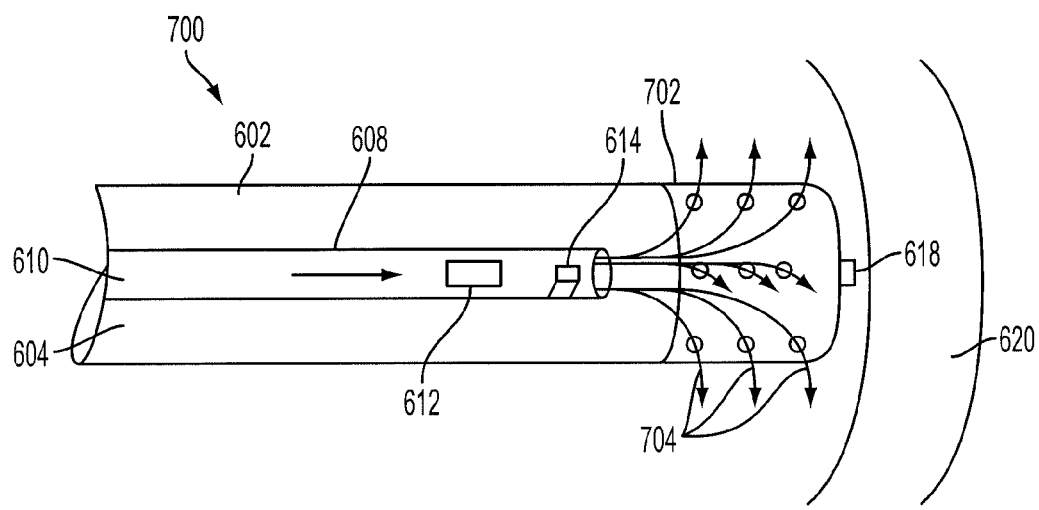
FIG. 7 is a side view of one embodiment of an ablation device having an open loop flow pattern.

FIG. 7 illustrates another embodiment of an ablation device having an open-loop flow, as opposed to the closed-loop flow shown in FIG. 6. As shown in the figure, the device 700 can include several components common to the device of FIG. 6. For example, the device 700 can include an elongate body 602 having an inner lumen 604, a delivery lumen 608 disposed within the inner lumen 604 and having its own inner lumen 610, a heating assembly 612 and temperature sensor 614 housed within the inner lumen 610, and, in some embodiments, one or more additional temperature sensors, such as the temperature sensor 618.

The device 700 differs from the device 600 in that it includes an ablation element 702 having a plurality of outlet ports or pores formed therein that communicate between an inner surface and an outer surface of the ablation element. As a result, when fluid is introduced into the inner lumen 604 adjacent to the ablation element 702, the fluid can flow through the ablation element 702 and into the body cavity surrounding the device 700. The resulting open-loop flow pattern is illustrated by flow direction arrows 704. As a result of the open-loop flow pattern, the device 700 can, in some embodiments, remove the separate delivery lumen 608 and simply pump fluid in a single direction through the inner lumen 604 of the elongate body 602. In such an embodiment, the heating assembly and any temperature sensors can be disposed within the inner lumen 604 of the elongate body 602.

The devices shown in FIGS. 6 and 7 can both be used to administer ablation therapy that prevents the overheating of tissue while producing therapeutic treatment at greater depths than previously possible. In some embodiments, however, it can be preferable to utilize the closed-loop device 600 rather than the open-loop device 700. For example, in embodiments where the temperature of the fluid introduced from the delivery lumen 608 is sufficiently high (e.g., 70° C. and above), it can be undesirable to allow the fluid to flow into the bloodstream or tissue surrounding the ablation device. Fluid at that temperature can, in some cases, damage tissue or cause blood clots to form. Accordingly, it can be desirable to collect the heated fluid at the proximal end of the device, rather than introduce the fluid into the patient's body. This can vary by location and specific anatomy of the treatment site, however. For example, areas having high blood flow may be able to dissipate the high temperature fluid without risk of developing complications.

The devices described above can be utilized in a variety of procedures requiring ablation of tissue within the body. For example, the devices and methods disclosed herein can be particularly useful in cardiac ablation. Procedures for the treatment of atrial fibrillation and atrial flutter, such as the Maze Procedure, often require ablating a large amount of the cardiac anatomy in locations where the tissue walls have variable thickness. The methods and devices of the present invention allow operators to ablate a variety of tissue geometries using a minimum level of RF power and without overheating tissue at any depth.

For example, in ablating a thicker wall of the myocardium, a device similar to the device 600 can be inserted into a patient's body via an access port or other opening formed through one or more layers of tissue, or via a natural orifice (i.e., endoscopically). The device can subsequently be delivered to any treatment site within the body directly, or using existing passageways within the body (e.g., passing the device into the heart through a patient's blood vessels). Once in the vicinity of a desired treatment site, the ablation element of the device can be positioned using the aid of sensing electrodes or other positioning instruments, and the distal tip of the ablation element can be pressed against a tissue wall at a particular location. Further, in many embodiments the elongate body and/or ablation element can have a blunt distal end, such that the elongate body and/or ablation element can be pressed against a tissue wall without penetrating through the tissue. Following positioning, RF energy can be delivered into the tissue wall while fluid is simultaneously delivered through the elongate body, e.g., through a delivery lumen. The fluid can be heated by a heating assembly positioned in a distal portion of the elongate body, e.g., within a distal portion of the delivery lumen. The fluid can contact the ablation element and either flow through ports formed in the ablation element or flow back up to the proximal end of the elongate member to convect heat away from the ablation element. The delivery of the heated fluid can effectively regulate the temperature of the ablation element to match that of the heated fluid. The controlled and elevated operating temperature can allow ablation therapy to be conducted using an efficient level of RF power, and the heating of tissue above a threshold level, e.g., 100° C., can be avoided.

The above exemplary embodiments describe the treatment of cardiac tissue. While this is one contemplated use, the methods and devices of the present invention can be equally adapted for use in other areas of a patient's body. As such, the devices described herein can be formed in a variety of sizes and materials appropriate for use in various areas of a patient's body.

In addition, those that are knowledgeable in the art will recognize that the heating mechanism for producing hyperthermia within the target tissue sufficient to destroy it can include other forms of energy. Ultrasonic vibrational energy is known to be absorbed by tissue and converted to heat, as is microwave and light wave electromagnetic energy. Alternative embodiments may employ ultrasonic transducers, microwave antennas, or light wave diffusers as emitters disposed in the distal end of an elongate body. Light wave electromagnetic energy can fall in a range spanning visible, near-infrared, infrared, and far-infrared radiation, and can be generated by filaments, arc lamps, lasers of various forms (e.g., diodes, semiconductors, or pumps), or by other means. Similarly, the heating assembly or element described above can have a variety of forms, including a resistive wire for heating the fluid through conduction. Regardless of the type of ablation element utilized, the injection of heated liquid into the elongate body adjacent to the ablation element can aid in regulating its temperature, and using saline heated above room temperature can increase the efficiency of the ablation therapy and allow the use of lower RF power. It is also recognized that the devices described above can be delivered to a treatment site using any standard medical delivery device, depending on the tissue to be treated. Exemplary alternative embodiments can include metallic or nonmetallic needle bodies, sheaths, or introducers.

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

For example, the devices disclosed herein may be disassembled partially or completely. In particular, the elongate body 602 of the medical device 600 shown in FIG. 6 may be decoupled from any control handle or other connected component, or the elongate body 602 can be separated from the ablation element and/or any delivery lumen extending therethrough. Similarly, the heating assembly or element 612 and the temperature sensor 614 can be separated from the delivery lumen 608 and/or elongate body 602 for cleaning and/or replacement. These are exemplary disassembly steps only, as any component of the device can be configured to separate from the device for cleaning and/or replacement.

Preferably, the devices described herein will be processed before surgery. First, a new or used instrument can be obtained and, if necessary, cleaned. The instrument can then be sterilized. In one sterilization technique, the instrument is placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility.

In many embodiments, it is preferred that the device is sterilized. This can be done by any number of ways known to those skilled in the art including beta or gamma radiation, ethylene oxide, steam, and a liquid bath (e.g., cold soak). In certain embodiments, the materials selected for use in forming components such as the elongate body may not be able to withstand certain forms of sterilization, such as gamma radiation. In such a case, suitable alternative forms of sterilization can be used, such as ethylene oxide.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

The invention claimed is:

1. A method of ablating tissue, comprising:
positioning a blunt distal portion of an elongate body in contact with tissue;
delivering ablative energy to the tissue through an ablation element on the blunt distal portion of the elongate body;
delivering fluid from a proximal end to a distal end of the elongate body through a delivery lumen within an inner lumen of the elongate body;
returning fluid from the distal end to the proximal end of the elongate body through a return lumen within the inner lumen of the elongate body without releasing the fluid into tissue;
heating the fluid to a temperature greater than 37° C. and less than 100° C. using a heater element disposed in a distal portion of the elongate body;
wherein heating the fluid using a heater element includes passing electrical current through at least one wire that extends through at least one spacer to pass energy through fluid flowing through the inner lumen of the elongate body;
wherein the at least one spacer is configured to maintain a position of the at least one wire within he inner lumen of the elongate body, and
wherein heating the fluid using a heater element includes passing electrical current from a first power source between a single wire and a conductive elongate body.

2. The method of claim 1, wherein the blunt distal portion of the elongate body does not penetrate the tissue.

3. The method of claim 1, wherein the ablation element is positioned at the distal end of the elongate body and adjacent to the tissue.

4. The method of claim 1, wherein the heater element is disposed within the inner lumen to heat the fluid.

5. The method of claim 1, further comprising detecting the temperature of the tissue in contact with the blunt distal portion of the elongate body using a temperature sensor disposed on a distal end of the elongate body.

6. The method of claim 1, further comprising detecting the temperature of the fluid delivered through the elongate body using a temperature sensor disposed distal to the heater element.

7. The method of claim 6, further comprising adjusting an output level of any of the ablation element and the heater element to maintain the temperature of the ablation element above 37° C. and below 100° C.

8. The method of claim 1, wherein delivering ablative energy to the tissue through an ablation element includes passing electrical current from a second power source between the conductive elongate body and a collector electrode positioned outside the inner lumen.

9. The method of claim 1, wherein the return lumen is defined by the annular space between the delivery lumen and an inner wall of the elongate body inner lumen.

10. The method of claim 1, wherein the delivery lumen and the return lumen are each separate hollow tubes disposed within the inner lumen of the elongate body.

11. The method of claim 1, wherein the delivery lumen is positioned within the inner lumen of the elongate body such that it does not move with respect to the elongate body.

12. The method of claim 1, wherein the delivery lumen floats freely within the inner lumen of the elongate body.

13. A method of ablating tissue, comprising:
positioning a blunt distal portion of an elongate body in contact with tissue;

delivering ablative energy to the tissue through an ablation element on the blunt distal portion of the elongate body;

delivering fluid from a proximal end to a distal end of the elongate body through a delivery lumen within an inner lumen of the elongate body;

returning fluid from the distal end to the proximal end of the elongate body through a return lumen within the inner lumen of the elongate body without releasing the fluid into tissue;

heating the fluid to a temperature greater than 37° C. and less than 100° C. using a heater element disposed in a distal portion of the elongate body;

wherein heating the fluid using a heater element includes passing electrical current through at least one wire that extends through at least one spacer to pass energy through fluid flowing through the inner lumen of the elongate body;

wherein the at least one spacer is configured to maintain a position of the at least one wire within the inner lumen of the elongate body; and wherein heating the fluid using a heater element includes passing electrical current through two wires that extend through two spacers.

14. The method of claim 13, wherein the blunt distal portion of the elongate body does not penetrate the tissue.

15. The method of claim 13, wherein the ablation element is positioned at the distal end of the elongate body and adjacent to the tissue.

16. The method of claim 13, further comprising detecting the temperature of the tissue in contact with the blunt distal portion of the elongate body using a temperature sensor disposed on a distal end of the elongate body.

17. The method of claim 13, further comprising detecting the temperature of the fluid delivered through the elongate body using a temperature sensor disposed distal to the heater element.

18. The method of claim 17, further comprising adjusting an output level of any of the ablation element and the heater element to maintain the temperature of the ablation element above 37° C. and below 100° C.

19. The method of claim 13, wherein the return lumen is defined by the annular space between the delivery lumen and an inner wall of the elongate body inner lumen.

20. The method of claim 13, wherein the delivery lumen and the return lumen are each separate hollow tubes disposed within the inner lumen of the elongate body.

21. The method of claim 13, wherein the delivery lumen is positioned within the inner lumen of the elongate body such that it does not move with respect to the elongate body.

22. The method of claim 13, wherein the delivery lumen floats freely within the inner lumen of the elongate body.

* * * * *